US006928672B2

(12) United States Patent
Pastyr et al.

(10) Patent No.: US 6,928,672 B2
(45) Date of Patent: Aug. 16, 2005

(54) PATIENT POSITIONING AND TRANSPORT SYSTEM

(76) Inventors: Otto Pastyr, Mannheimer Weg 6, D-69181 Leimen (DE); Gernot Echner, Panoramastrasse 13, D-69257 Wiesenbach (DE); Wolfgang Schlegei, In der Aue 22/1, D-69118 Heidelberg (DE); Volker Sturm, Störchelberg 9, D-69168 Wiesloch-Schatthausen (DE); Harald Treuer, Lindenweg, D-50858 Köln (DE)

( * ) Notice: Subject to any disclaimer, the term of this patent is extended or adjusted under 35 U.S.C. 154(b) by 0 days.

(21) Appl. No.: 10/478,595
(22) PCT Filed: May 10, 2002
(86) PCT No.: PCT/EP02/05129
§ 371 (c)(1), (2), (4) Date: Nov. 24, 2003
(87) PCT Pub. No.: WO02/098294
PCT Pub. Date: Dec. 12, 2002

(65) Prior Publication Data
US 2004/0143905 A1 Jul. 29, 2004

(30) Foreign Application Priority Data
Jun. 5, 2001 (DE) .......................................... 101 27 210

(51) Int. Cl.⁷ ................................................ A61G 7/14
(52) U.S. Cl. ........................... 5/81.1 HS; 5/86.1; 5/601
(58) Field of Search ........................ 5/81.1 R, 81.1 HS, 5/86.1, 601; 378/209

(56) References Cited

U.S. PATENT DOCUMENTS

| 4,105,923 A | | 8/1978 | Hynes |
| 4,873,732 A | * | 10/1989 | Perez ...................... 5/81.1 HS |
| 5,077,780 A | * | 12/1991 | Lee, Jr. ....................... 378/196 |
| 5,111,541 A | | 5/1992 | Wagner |
| 5,475,884 A | * | 12/1995 | Kirmse et al. .................. 5/601 |
| 5,493,741 A | * | 2/1996 | Baer ............................ 5/86.1 |
| 5,842,987 A | | 12/1998 | Sahadevan |
| 6,205,347 B1 | | 3/2001 | Morgan |
| 6,484,332 B2 | * | 11/2002 | Korver et al. ............. 5/81.1 R |
| 6,640,364 B1 | * | 11/2003 | Josephson et al. ............. 5/601 |

FOREIGN PATENT DOCUMENTS

| DE | 28 12 074 | 5/1979 |
| DE | 42 24 036 | 5/1993 |
| DE | 43 30 606 | 7/1994 |
| EP | 0 047 958 | 3/1982 |

* cited by examiner

Primary Examiner—Michael Trettel
(74) Attorney, Agent, or Firm—Paul Vincent (57) ABSTRACT

The invention relates to a patient positioning and transport system comprising a transportable stretcher (1) and a cart (2) for transporting the stretcher (1) with the patient. The stretcher (1) can be removed from the cart (2) to be placed on a diagnosis or treatment station (4). A patient positioning and transport system of the aforementioned type should be designed as to avoid, to the greatest possible extent, repositionings of the patient between separate diagnosis or treatment stations (4). Towards this end, at least one adapter plate (3) that can be assigned to the stretcher (1) is provided, whereby the stretcher (1), the adapter plate (3) and the cart (2) can be joined to another and are configured in such a manner that the stretcher (1) with the patient can be transferred from the cart (2) to various, differently designed diagnosis or treatment stations (4) and back.

49 Claims, 5 Drawing Sheets

PATIENT POSITIONING AND TRANSPORT SYSTEM

This application is the national stage of PCT/EP02/05129 filed on May 10, 2002 and claims Paris Convention priority of DE 101 27 210.3 filed Jun. 5, 2001.

BACKGROUND OF THE INVENTION

The invention concerns a patient positioning and transport system with a transportable stretcher and a cart for transporting the stretcher along with the patient, wherein the stretcher can be removed from the cart and be disposed on a diagnosis or treatment station.

The underlying problem of the invention concerns the fact that different diagnosis or treatment stations each have their own stretchers. Patients who must be diagnosed and treated sequentially at several stations must be positioned onto the stretchers of those stations and back onto the transport cart. Conventional carts may have stretchers which can be removed from the cart and placed onto an operation table. This however, does not solve the problems involved when different diagnosis or treatment stations of different construction must be visited which do not permit disposition of the above-mentioned stretcher.

In particular, many stations must often be passed for stereotactic diagnoses and treatment. The treatment region must usually be initially defined using an imaging device, i.e. computer tomography, e.g. with radiographs, or magnetic resonance imaging (also called nuclear magnetic resonance tomography). This is often followed by angiography for detecting the position of the blood vessels. Therapy is started following stereotactic therapy planning which, for its part, may require hours to evaluated the detected data and plan therapy in three-dimensional space. Operations must be carried out with high spatial precision. Treatments of this type include e.g. radiation, removal of biopsies, introduction of radioactive seeds, laser treatment etc. These diagnosis and treatment processes are often one-time proccedures and the spatial conditions of diagnosis must be reproducible with high accuracy using image monitoring up to the operation in order to ensure that diseased tissue can be precisely treated by the therapy while healthy tissue is protected. If the treatment regions are close to sensitive tissues such as the spinal cord, nerves etc. the required accuracy is often in the millimeter region. Towards this end, bearing and positioning systems were developed having shells which are adapted to the body or with a head ring which is fixed to the head via holding stops and optionally fixed to bones such as spinal vertebrae. These positioning systems thereby have a fixed relationship to the corresponding body part and have their own markings which are detected to provide coincidence of positions for therapy.

For diagnosis and treatment in several stations, repositionings of the patient are time-consuming and tiring for the patient and the staff, and also involve the risk that a positioning system changes its location relative to the corresponding body part, thereby losing the fixed calibrating relationship. In this case, the positioning system would have to be refixed and the entire procedure, starting with imaging, must be repeated. It would be even worse if such a positioning error went unnoticed, since spatial inaccuracies endanger the success of the therapy and could cause damage to the patient.

It is therefore the underlying purpose of the present invention to develop a patient positioning and transport system which substantially avoids patient repositionings between individual diagnosis or treatment stations.

This object is achieved for a patient positioning and transport system of the above-mentioned type in that the stretcher has at least one associated adaptor plate, wherein the stretcher, the adapter plate and the cart can be connected to each other and are designed such that the stretcher can be moved along with the patient from the cart to various structurally different diagnosis and treatment stations, and back.

SUMMARY OF THE INVENTION

The invention is based on the finding that, in view of the plurality of the above-mentioned diagnosis or treatment stations and the continuous new developments in these stations, it is not sufficient if only the stretcher can be removed from a cart and be disposed e.g. on the operating table. The most differing conditions at the individual diagnosis and treatment stations must be taken into account including spatial conditions, the apparatus structure and the respective construction as well as physical conditions requiring materials which do not disturb the devices. It is therefore not possible to design a stretcher which can be removed from a cart which simultaneously satisfies all these numerous requirements. These requirements must, however, be met in order to allow the patient on the stretcher to pass at least all diagnosis or treatment stations between imaging and termination of the therapy without being repositioned. The invention therefore provides for at least one adapter plate associated with the stretcher. The stretcher is supported on the adapter plate, and optionally one or more further adapter plates are disposed therebelow. These are all positioned on the cart such that the stretcher can be removed separately, or with one or more adapter plates to be disposed in the respective diagnosis or treatment station. The separate use of the stretcher is advantageous in diagnosis or treatment stations having space and/or diagnosis or treatment stations with stringent requirements with regard to the physical properties of the stretcher. The underlying adaptor plate may occupy a certain amount of space but must not satisfy the high requirements of the stretcher with regard to the materials from which it is produced, rather is e.g. adapted to the existing apparatus of further diagnosis or treatment stations such as inserting direction or the mechanisms for inserting the stretcher. In this fashion, further adapter plates may be provided through which the stretcher with intermediate adapter plates can be associated with further diagnosis or treatment stations, wherein the design of the respective adapter plate takes into account the requirements dictated by the respective diagnosis or treatment station. Embodiments and further developments of the invention provide corresponding examples. The invention also concerns optimised adjustment of diagnosis or treatment stations for easy and shock-free movement of the stretcher onto the diagnosis or treatment station and back, and suitable achievement of compatibility. This may be effected by modifying the diagnosis or treatment station or by adding further adapter parts. Such measures are also described in further developments of the invention.

In one advantageous embodiment mentioned above, the stretcher has at least one associated adapter plate with the stretcher and adapter plate being designed such that the stretcher can be moved, separately and also together with the adapter plate, from the cart to different diagnosis or treatment stations and back. Such embodiments are intended to provide compatibility with all diagnosis or treatment stations for possible diagnosis and treatment by satisfying the requirements of a plurality of such stations. The adapter plates optimally fulfil the required universality. Movement of the stretcher to the diagnosis and treatment stations could, of course, be effected exclusively with adapter plates.

The stretcher and/or one of the adapter plates disposed there below may be designed to permit different types of movement of the stretcher in or onto the respective diagnosis or treatment station.

At least one of the positioning mechanisms of the stretcher or of at least one adapter plate may be designed to allow movement and exact positioning through lifting and lowering. Alternatively, at least one of the positioning means of the stretcher or of the at least one adapter plate may be designed such that movement is possible through displacement in a longitudinal direction. Furthermore, at least one of the positioning means of the stretcher or of the at least one adapter plate can be designed such that movement is possible through displacement in a transverse direction. Since the different diagnosis and treatment stations must meet different requirements, it is generally advisable to design the stretcher with adapter plates such that all three above-mentioned possible movements of the stretcher onto a diagnosis or treatment station are integrated in the patient positioning and transport system.

The bearings are advantageously designed such that a fixed connection can be produced. The stretcher and at least one adapter plate may be provided with positioning devices for defined, secure arrangements. In this fashion, the stretcher can be fixed to the desired number of adapter plates and to the respective diagnosis or treatment station to permit positioning of the stretcher with one or more adapter plates onto or into a diagnosis or treatment station. The cart may also be advantageously provided with positioning devices for defined, secure arrangement. This ensures sufficient securing of the patient during transport and/or secure positioning should the cart as such be inserted into a diagnosis or treatment station. Advantageously, the at least one position which permits lifting of the stretcher is additionally secured against unintentional lifting. In particular, during transport of the patient with the cart, such inadvertent lifting must be prevented e.g. when different levels must be overcome in corridors or at elevators.

Further various requirements take into consideration the physical requirements of the different diagnosis or treatment stations. For this reason, the materials of the individual components of the patient positioning and transport system are selected such that disturbances of diagnosis or treatment stations are eliminated. The components which interact with the respective diagnosis or treatment stations which are sensitive to such influences must thereby be properly designed. It is e.g. advantageous if the cart and the at least one adaptor plate consist of non-magnetic or only weakly magnetic materials to prevent magnetic forces from pulling parts into the magnetic resonance tomograph when the cart with stretcher and adaptor plates is proximate thereto.

If the stretcher is disposed in a magnetic resonance tomograph, it must be made from non-magnetic and non-conducting materials to avoid inadmissible imaging distortions. In this case, the components which are not moved into the magnetic resonance tomograph, must, of course, not have these properties. The materials of these components of the system must only be designed such that the stretcher can be disposed in the magnetic resonance tomograph without causing disturbances. A further requirement may be that the stretcher and the adaptor plate supporting the stretcher contain no metal. This embodiment is appropriate for moving the stretcher with underlying adapter plate into a computer tomography device. These two components must be designed such that they have no negative influence on the images. For arrangement in an irradiation device, the stretcher or one of its adapter plates may not contain any materials which influence the treatment radiation. Of course, further requirements, e.g. for further adapter plates, are feasible depending on the type and requirements of diagnosis or treatment stations.

The above-mentioned elements of the patient positioning and transport system may be designed such that they are compatible with existing diagnosis or treatment stations. Of course, the patient positioning and transport system may also include components of a specific diagnosis or treatment station as required to ensure easier transport of the stretcher or more exact patient positioning. For this reason it is proposed that at least one of the diagnosis or treatment stations is designed such that an adapter plate can be securely disposed therein. An adapter plate may be a base plate which can be securely disposed on the cart but can be lifted therefrom. In an adventageous embodiment, the cart is designed such that it can be moved, with the base plate, over a diagnosis or treatment station, wherein the latter has a further position and height adjustment such that the base plate can be lifted from the cart and newly disposed. The cart can be removed from the diagnosis or treatment station after the base plate is lifted. This diagnosis or treatment station also advantageously comprises a positioning device to ensure that positioning is maintained during transfer. The diagnosis or treatment station may be an operating table having the above-mentioned height adjustment. For use on such an operating table, the base plate may be designed like other operating table plates e.g. made from electrically conducting hard board (a composite material of high stability which consists of paper and resin layers and obtains electric conductivity through graphite admixture) as is conventionally used in various medical treatments. Should the intermediate plate be made from carbon, it slides very well on the hard board base plate. The height adjustability of the operating table advantageously permits adjustment of the patient to the optimum working height of the treating physician.

The stretcher may be designed to be displaceable in a longitudinal direction as is advantageous for transport to diagnosis or treatment stations having a corresponding positioning, in particular when these are formed to cooperate with the longitudinally displaceable position mechanisms of the stretcher such that the stretcher can be inserted directly from the cart into the diagnosis or treatment station. The longitudinally displaceable positioning means is advantageously effected to prevent lifting of the stretcher. At least one side thereof may be designed as dove-tailed or T-shaped grooved guidance. The diagnosis or treatment station, e.g. a magnetic resonance tomograph often has a tubular region into which the patient must be inserted. The longitudinally displaceable position mechanism is thereby correspondingly matched to the position mechanism of the diagnosis or treatment station.

As mentioned above, the stretcher must be of non-magnetic and non-conducting materials for introduction into a magnetic resonance tomograph. The fact that the stretcher can be directly inserted into the magnetic resonance tomograph without an adapter plate is advantageous since the space therein is very limited and the height of the stretcher to be introduced should be small. It is therefore also advantageous to make the stretcher very flat. A fiber-reinforced, sandwich construction is preferred. To meet these spatial and physical requirements, the stretcher may be made from Kevlar®, preferably of two harder layers sandwiching a central plastic foam. The stretcher is designed such that it can be introduced into the magnetic resonance tomograph without adapter plate. Only the stretcher must thereby meet the very stringent physical requirements, i.e. of being absolutely non-magnetic and non-conducting, and not the adapter plate as well.

Conventional magnetic resonance tomographs generally have a stretcher. To ensure that it does not have to be dismounted for use of the inventive stretcher, the inventive stretcher is sufficiently flat that it can be placed over the stretcher of a magnetic resonance tomograph, wherein the position mechanism of the magnetic resonance tomograph is adapted and designed for this purpose. The magnetic resonance tomograph stretchers very often have longitudinal grooves along the edges for accessories—often in the form of dove-tailed grooves—which can be used for positioning. If there are no such grooves, such grooves can advantageously be provided in the magnetic resonance tomograph stretcher to be able to slide the inventive stretcher onto that magnetic resonance tomograph stretcher. The invention also concerns a stretcher which can be introduced separately and characterized by association with at least one adapter plate to permit use in other diagnosis or treatment stations, as is requested to achieve the inventive object.

At least one positioning device can preferably be attached to the stretcher to fix body parts which are to be treated. This is possible since, in contrast to the conventional stretchers, repositioning of the patient is no longer required and these positioning devices are not carried along and mounted to new stretchers when the patient is repositioned. The fact that the patient stays on the stretcher, together with the positioning devices, during the entire diagnosis and treatment, i.e. from imaging to the end of the therapy, is the substantial advantage of the inventive design of a stretcher with associated adapter plates and avoids the need to reposition the patient.

One example for such a positioning device is a head holder ring, with the ring being fixed to the head of the patient using holding stops or other positioning devices. A head holder mounting is disposed at the end of the stretcher to attach this head holding ring to the stretcher. In this case, the head holder mounting may serve as a positioning stop at the end of a longitudinal displacement e.g. when the stretcher is inserted into a magnetic resonance tomograph. The head holder mounting is then preferably structured e.g. to permit the head holder ring to be positioned such that a head held therein comes to rest in a central region of the magnetic resonance tomograph, despite the positioning of the stretcher above the stretcher of the magnetic resonance tomograph, since the best quality images are generated in this region.

In a further development, an adapter plate is provided between the stretcher and base plate which is designed as an intermediate plate. It may be positioned such that it can be displaced transverse to the base plate. This is suitable when a patent is to be moved transversely into diagnosis or treatment stations as is often the case with angiography and computer tomography stations since many regions in hospitals have very limited space and devices are used having transverse insertion of the patients. The transversely displaceable position suitably consists of guides which prevent lifting of the intermediate plate, and end stops for positioning. The heights of the guides are suitably matched such that the stretcher with adapter plate can be inserted directly from the cart into the diagnosis or treatment station.

Transversely displaceable positioning means are suitably designed to permit displacement to one side and with end stops on the other side. The stretcher is thereby held at one side and can be moved towards the other side into a diagnosis or treatment station. It is also suitable when the transversely displaceable positioning means has V-shaped guides which widen towards the outside and taper towards the end stop. This permits easy threading of guiding elements into the guides without having to open the guides to displace the stretcher. In a particularly advantageous design, each side has at least two guides with end stops and the end stops are generated by cooperation between the end regions of the guides and guiding and holding bolts. The intermediate plate can advantageously be optionally displaced to the one or the other side through removable and fixable guiding and holding bolts. In this fashion, the side for displacement can be selected by fastening the removable and fixable guiding and holding bolts on the one or the other side.

The above-mentioned further developments are particularly advantageous when a diagnosis or treatment station is designed such that it is at the same height as the base plate of the stretcher disposed on the cart and when the diagnosis or treatment station has guiding and holding bolts such that the stretcher is positioned there through end stops after transverse displacement. In this fashion, transverse displacement in diagnosis and treatment stations is provided irrespective of whether displacement to the left or right is required. Such displacement permits displacement of the stretcher from the end stops on the cart to the end stops of the diagnosis or treatment station.

Further embodiments of the invention concern the cart. The front side of the cart may have a portal-like opening such that it can be moved over a diagnosis or treatment station together with the stretcher and the at least one adapter plate. With respect to this transfer, reference is made to the above-mentioned height adjustment of a diagnosis or treatment station cooperating with the cart.

At least the head end of the cart has springs which, in particular, for patients whose head is fixed in a head holder ring, serve to protect the patient from impact during transport. Good handling of the cart is ensured if it has a wheel brake and fixed travel direction for the front wheels. The rear wheels serve for safe and stable pushing of the cart. The cart may have a mechanism for adjustment to a height to move the stretcher into a diagnosis or treatment station for permitting easy displacement or other motion of the stretcher and patient.

Should the stretcher fail to fit all diagnosis or treatment stations despite corresponding design of the adapter plates, at least one further adapter part may be provided to permit disposition of the stretcher on a diagnosis or treatment station for which none of the adapter plates fits. Such an adapter part may constitute e.g. a support on an existing stretcher. This auxiliary means facilitates use with stretchers having completely different designs, in particular differently shaped depressions. Since it would be too demanding to design adapter plates for each stretcher designs (in particular for such depressions) it may be easier to provide a compensating adapter part for each case. This may be a very simple adapter part and consist of at least two support bars which can be connected to each other via an additional bar. The structure of the adapter part is stable and straightforward. It can be easily dismounted and requires little storage space. It can also be easily shaped in correspondence with the individual requirements. Interposing such an adapter part does not preclude arrangement of positioning means between the stretcher with adapter plates and the diagnosis or treatment station. The adapter part may comprise e.g. guiding and holding bolts to provide the diagnosis and treatment station with end stops. The stretcher can thereby be displaced from the cart to a diagnosis or treatment station in the manner described above.

The following additional developments refer to further embodiments of the operating table for the inventive purpose.

All four legs of the operating table may have a synchronous, electric height adjustment as well as a means which interrupts the power supply from the mains after each actuation of the height adjustment, and which connects it again only upon explicit command. This eliminates disturbance of sensitive electric devices by an applied voltage and personel cannot inadvertently forget to interrupt the power supply, since same is done automatically.

For mounting the stretcher and for operations and other treatment measures, the operating table can be advantageously disposed on a position fixation mounted to the floor to prevent horizontal displacement while permiting raising and lowering. The structure of the operating table is moreover very stable to guarantee safe positioning with respect to the floor.

The operating table may of course also contain means for testing e.g. the correctness of the positioning of the patient and/or the instruments. The operating table may be provided with vertical and horizontal X-ray cassette holders to be able to obtain further images of the positioning of the body part to be treated through appropriate radiographs.

If the head of the patient positioned on the stretcher is to be introduced into a narrow diagnosis or treatment station, as is sometimes the case for a Gantry or a C-shaped bracket of an X-ray device, it may be suitable to provide the stretcher and the at least one adapter plate with a tapering at the head end.

The various embodiments of the invention can be used in arbitrary combination. A larger number of adapter plates or replaceable adapter plates may be provided. With such replaceable adapter plates, the conditions of the respective hospital, i.e. the existing devices may be taken into consideration and the adapter plates to be delivered can be selected accordingly or be individually adjusted such that the inventive system is compatible with all existing devices. Existing diagnosis or treatment stations may be adjusted to the adapter plates or to the stretcher, if this is easier.

BRIEF DESCRIPTION OF THE DRAWING

The invention is explained below with reference to embodiments shown in the drawing.

DESCRIPTION OF THE PREFERRED EMBODIMENT

Figure 1:
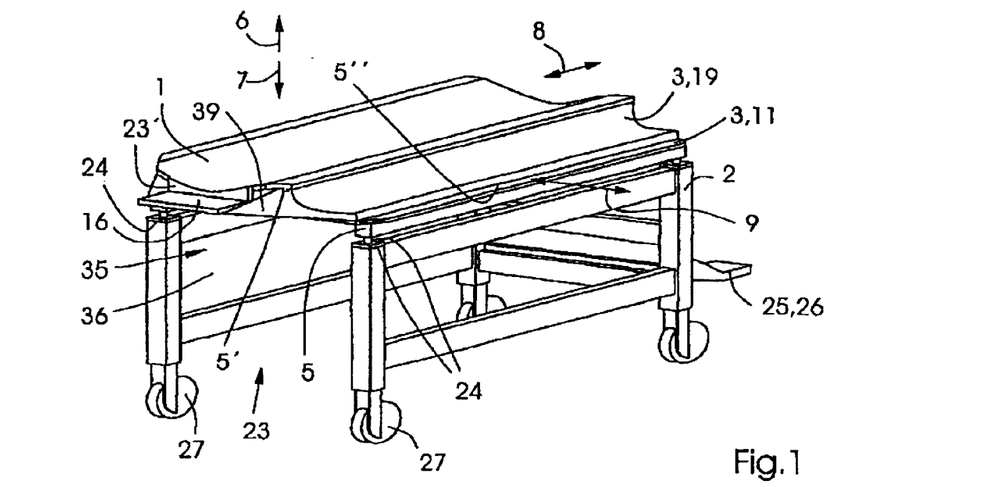
FIG. 1 shows an embodiment of the invention.
Figure 2:
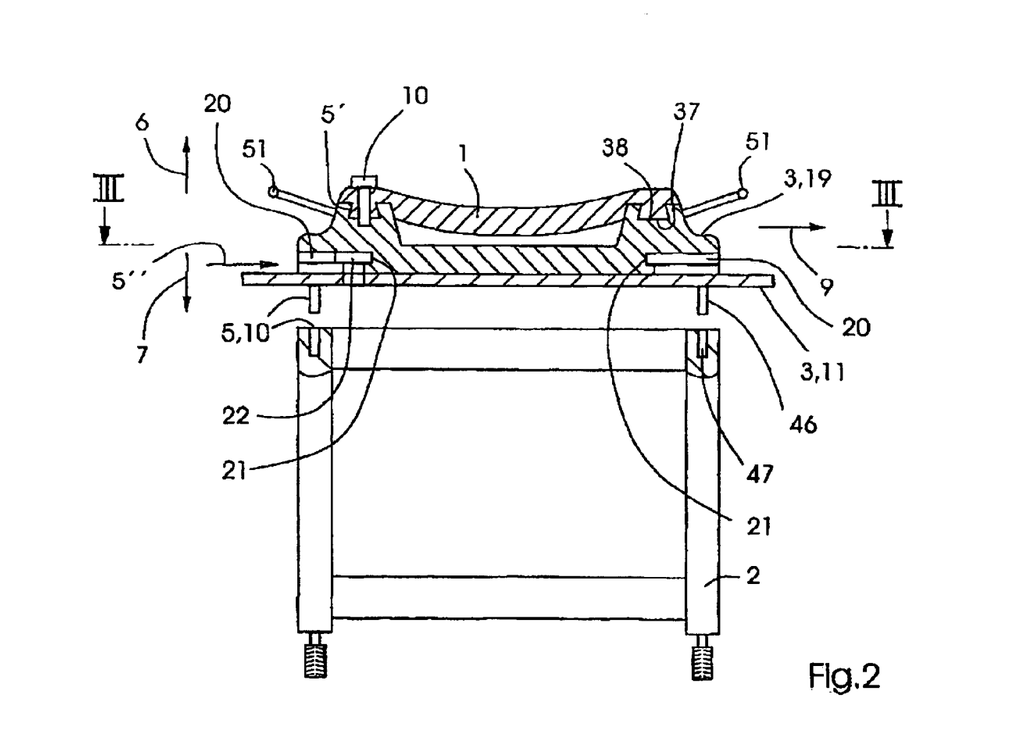
FIG. 2 shows a section through FIG. 1.

FIG. 1 shows an embodiment of the invention with a stretcher 1 disposed on a cart 2. The stretcher 1 has two associated adapter plates 3, namely a base plate 11 and an intermediate plate 19. The stretcher 1 is disposed on the intermediate plate 19 such that it can be displaced in a longitudinal direction (in the direction of arrow 8). The intermediate plate 19 is disposed on the base plate 11 to permit displacement in a transverse direction (in the direction of the arrow 9). The base plate 11 is disposed on the cart 2 in a secure fashion, wherein raising in the direction of the arrow 6 and lowering in the direction of the arrow 7 are possible. FIG. 2 shows the corresponding designs of the positioning means 5, 5', 5" which serve to move the stretcher 1 to different diagnosis or treatment stations 4.

Figure 5:
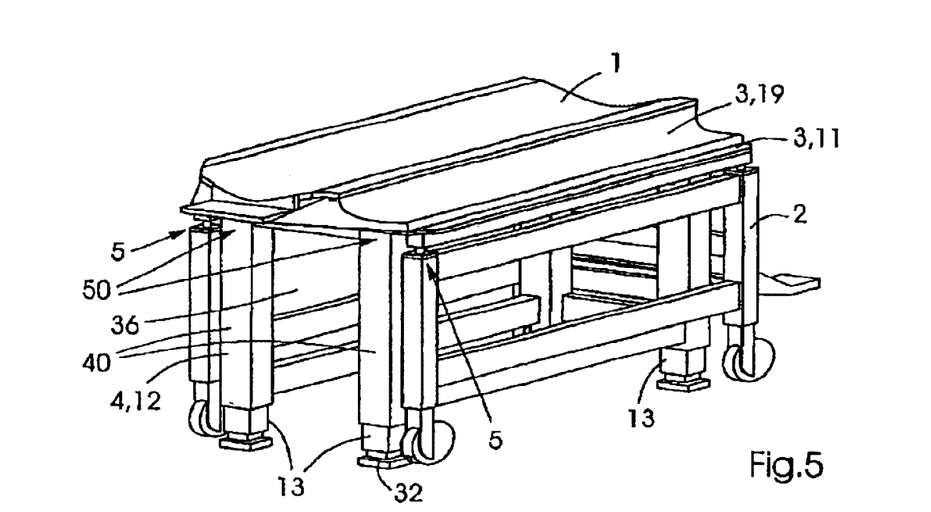
FIG. 5 shows inclusion of a correspondingly designed operating table in the inventive system.

FIG. 1 shows an embodiment of the cart 2 having a portal-like opening 36 at its front side 35 for movement over a diagnosis or treatment station 4 to position the stretcher 1 on this diagnosis or treatment station 4 (FIG. 5). Springs 24 are advantageously disposed at least at the head end 23 of the cart 2, in particular when the stretcher 1 has a head holder mounting 16 for a head holder ring 18, i.e. when the fixed patient must be protected from shocks during transport of the cart 23'. The head holder mounting 16 is at the head end 23' of the stretcher 1 which is preferably disposed at the head end 23 of the cart, i.e. at the front side 35.

FIG. 2 shows a section through FIG. 1. The positioning means 5,5',5" can be seen. The positioning means for the stretcher 1 on the intermediate plate 19 is formed as longitudinally displaceable positioning means 5'. The stretcher 1 has two sliding rails 38 which extend in two grooves 37 in the intermediate plate 19. At least one positioning means 5 of the grooves 37 and sliding rails 38 is designed as dove-tailed guide to prevent lifting off (direction 6) of the stretcher 1. Grooves 37 and sliding rails 38 are preferably formed on one side to fix the position, i.e. with minimum play and on the other side as loose position with larger play to prevent clamping. To prevent inadvertent displacement in the direction of the arrow 8, a positioning device 10 is provided which may be formed e.g. as insertable pin which exactly fixes a position.

A second transversely displaceable positioning means 5" is located between the intermediate plate 19 and the base plate 11. Towards this end, the intermediate plate 19 is provided with T-grooves 20 into which the guiding and holding bolts 22 can be inserted, wherein the exact positioning is obtained when the end stops 21 are reached. Two or more of these T-grooves 20 with guiding and holding bolts 22 may be provided. It is also thereby advantageous to provide a positioning device 10 to prevent inadvertent displacement which may also be an insertable locating pin 55. The preferred arrangement is shown in detail in FIGS. 3 and 4.

The two positioning means 5' and 5" are preferably matched with corresponding positioning means 5', 5" of diagnosis or treatment stations 4 in that they have also grooves 37 or T-shaped grooves 20 at the same height and same design such that with corresponding positioning of the cart 2, the patient with stretcher 1 can be moved to and from the diagnosis or treatment station 4.

A liftable positioning means 5 is also provided. It is located between the base plate 11 and the cart 2. It may consist e.g. of locating holes 47 into which bolts 46 engage. The latter may be joined to the base plate 11 and the locating holes 47 may be inserted into the cart 2 or vice versa. Other types of conventional connection may be envisioned. In a corresponding fashion, a further positioning means 50 should be provided (not shown) which engages counter pieces of the diagnosis or treatment stations 4 for matched transfer (FIG. 5).

The positioning means 5 is preferably provided with safety means (not shown) to prevent inadvertent lifting 6 during transport due to irregularities in the floor.

Figure 3:
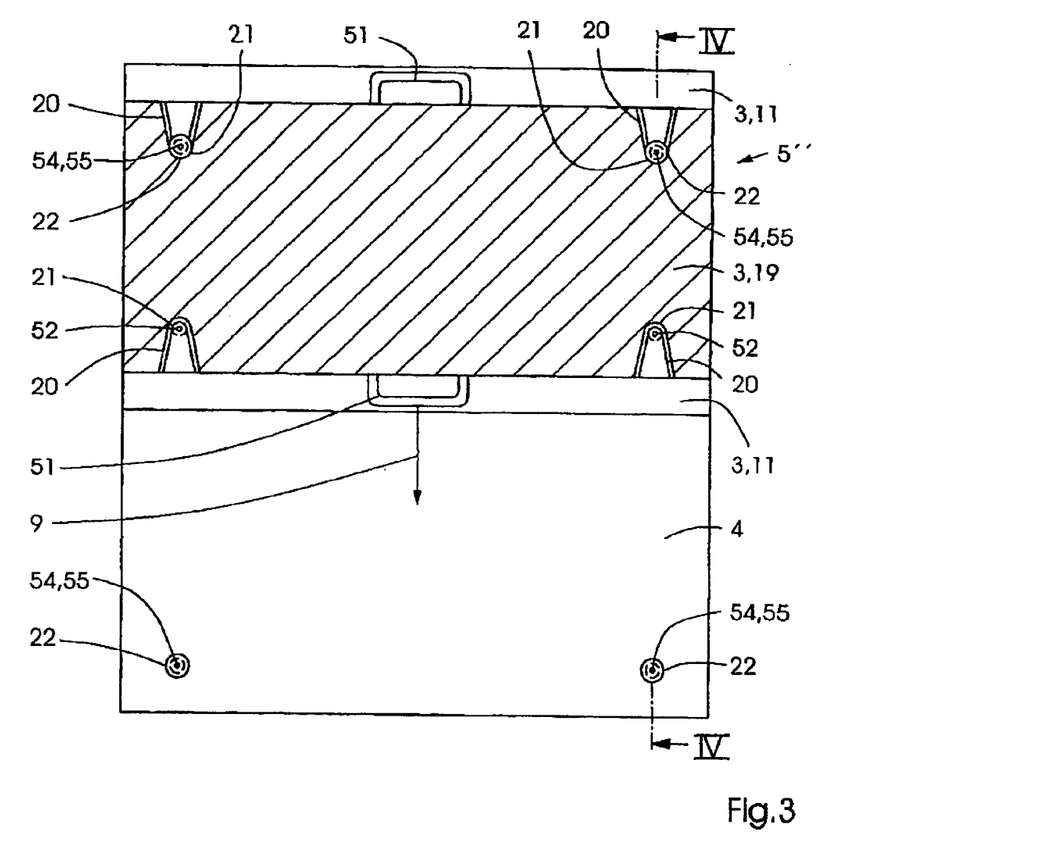
FIG. 3 shows a section III—III through FIG. 2.

FIG. 3 shows a section III—III through FIG. 2, illustrating a suitable embodiment of a longitudinally displaceable holder 5'. The guides 20 are V-shaped, wherein the inlet is wide and the guides 20 taper towards the end stops 21. These guides 20 are formed as T-shaped grooves and cooperate with guiding and holding bolts 22 which have a complementary mushroom-like shape. The end stops 21 are defined when the guiding and holding bolts 22 abut the ends of the guides 20.

This embodiment proposes four guides 20, two on each side. Of course, more guides 20 may be provided. The section is taken precisely at the upper side of the T-shaped groove 20 to clearly also illustrate how the guiding and holding bolts 22 generate the end stops 21 through cooperation with the ends of the T-shaped grooves 20. The guiding and holding bolts 22 are thereby disposed on the side opposite to the displacement direction 9 required to move the stretcher 1 to a diagnosis or treatment station 4. This diagnosis or treatment station 4 preferably also has guiding and holding bolts 22 which also serve as end stops 21 when the stretcher 1 reaches its final position through displacement 9 on the base plate 11 to the diagnosis or treatment station 4. In this fashion, the stretcher 1 is moved from a defined position on the cart 2 to the defined position on the diagnosis or treatment station 4.

The guiding and holding bolts 22 are screwed into threads at 52 in both sides in the base plate 11. The stretcher 1 can thereby be displaced to the left or to the right of the cart 2 depending on the design and arrangement of the diagnosis or treatment station 4. Locating holes 54 for locating pins 55 are also shown, which are worked into the guiding and holding bolts 22. Handles 51 on each side of the intermediate plate 19 serve to push the plate 19 towards the diagnosis or treatment station 4 in the direction shown, or in the opposite direction.

Figure 4:
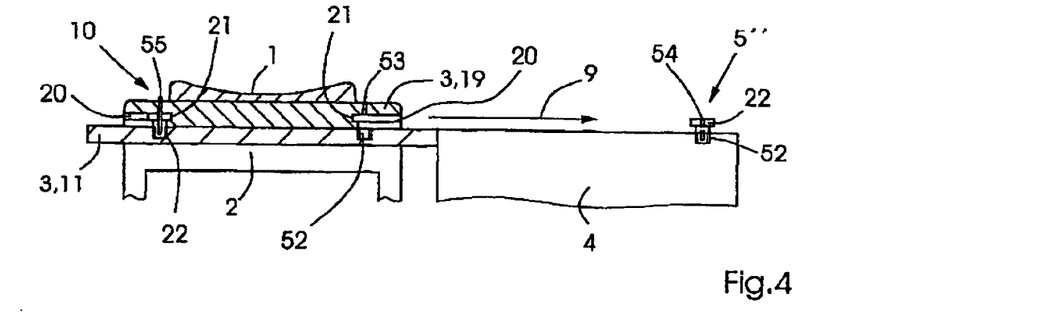
FIG. 4 shows a section IV—IV through FIG. 3.

FIG. 4 shows the same arrangement in section IV—IV. The region between the intermediate plate 19 and the stretcher 1 is shown in a simplified form and shows how the guiding and holding bolts 22 form the end stops 21 on the cart 2. At least one locating pin 55 is introduced as securing means for transport which is inserted through locating holes 53 of the intermediate plate 19 into the locating holes 54 of the guiding and holding bolts 22. When this locating pin 55 which serves as positioning device 10 is removed, the intermediate plate 19 with stretcher 1 can be displaced onto the diagnosis or treatment station 4 until the guiding and holding bolts 22 of the diagnosis or treatment station 4 engage in guides 20 on the right side of the intermediate plate 19 to encouter the end stops at the end of these guides 20. Locating pins 55 for positioning means 10 may also be inserted on the diagnosis or treatment station 4. Of course, the height of the base plate 11 must be exactly adjusted to the height of the diagnosis or treatment station 4 or vice versa.

FIG. 5 shows the integration of a correspondingly designed operating table 12 into the inventive system. The cart 2 described above with stretcher 1 and adapter plates 3 is moved over the operating table 12 via the portal-like opening 36. The height adjustment 13 integrated in the legs 40 of the operating table 12 is then actuated thereby lifting the base plate 11 with intermediate plate 19 and stretcher 1 from the cart 2 (shown already in FIG. 2). Towards this end, a further positioning means 50 is preferably provided which is integrated in the operating table 12 and the base plate 11 to fix the latter during transfer. When the height adjustment is finished such that the bolts 46 have been moved out of the locating holes 47 of the cart 2, and the positioning means 50 has engaged in a corresponding manner, the cart 2 may be removed and the stretcher 1 can be adjusted to any height on the operating table 12. The operating table 12 is preferably fixed to the floor 31 using a position fixation 32 (shown in detail in FIG. 5a). A fixation means is 41 mounted to the floor and engages a cavity 48 of the legs 40 of the operating table 12.

Figures 5A, 6:
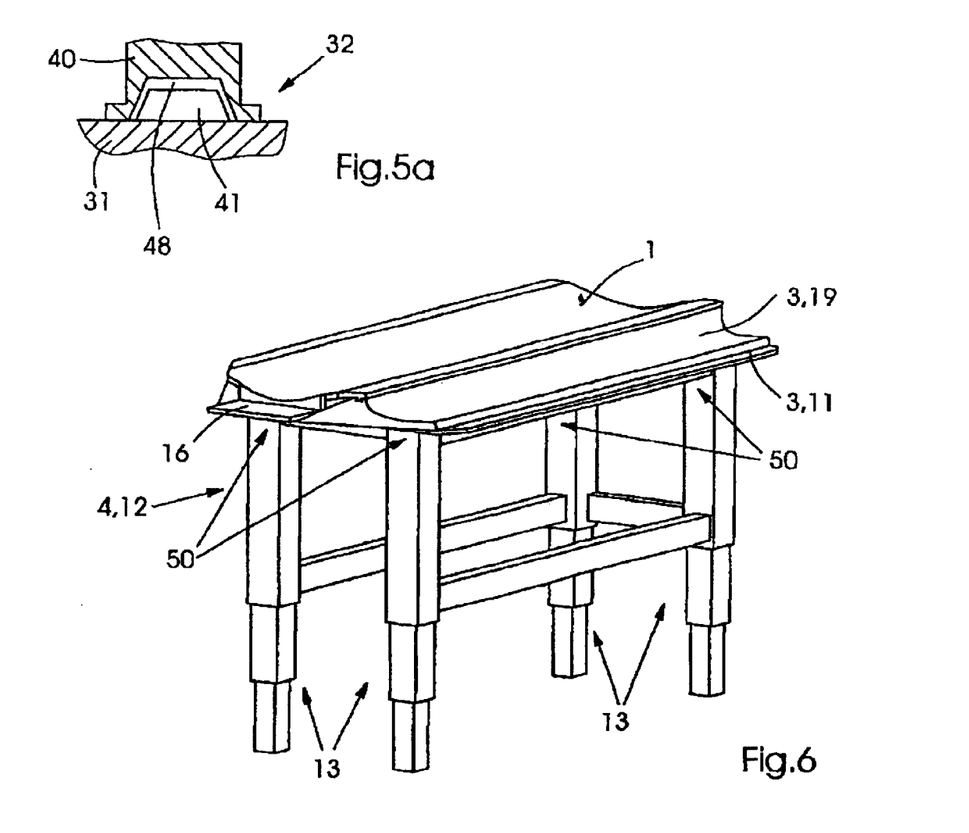
FIG. 5a shows a detail of FIG. 5.
FIG. 6 shows an operating table with stretcher and adapter plates.

FIG. 6 shows the operating table 12 with a stretcher 1 which is precisely fixed thereon via the base plate 11 and the further positioning means 50. The height adjustment 13 thereby serves to adjust the stretcher 1 to a height which is optimum for the physician. This is an additional benefit of the above-described height adjustment 13. The exact positioning of the patient on the operating table 12 is particularly important for operations where a defined target must be addressed from a defined inserting direction by means of a stereotactic handling device such as an adjustable arm.

Figure 7:
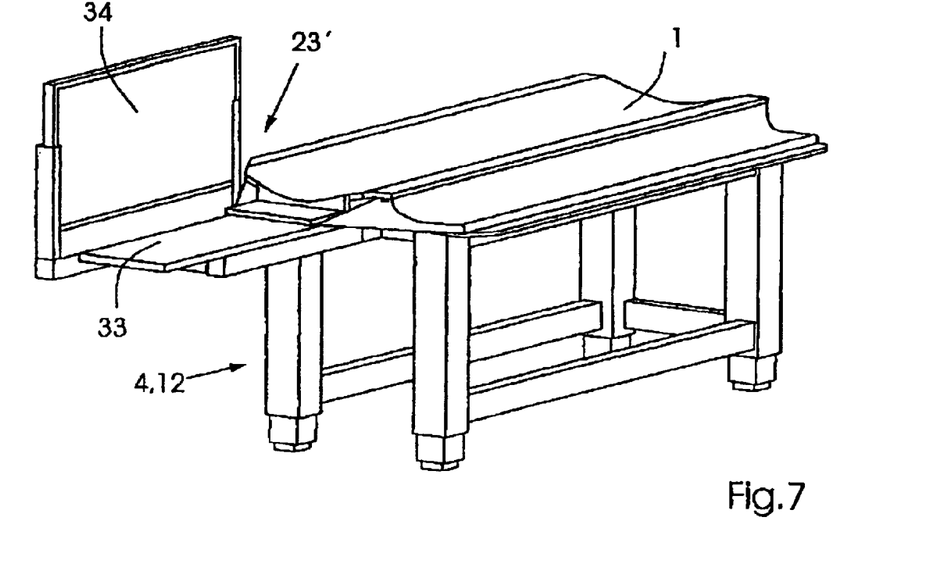
FIG. 7 shows an operating table with an auxiliary means.

FIG. 7 shows an operating table 12 with an auxiliary means. The head end 23' has a vertical X-ray cassette holder 33 and a horizontal X-ray cassette holder 34 to verify, by a radiograph, the exact position of the patient and/or of the instruments before operational start. These X-ray cassette holders 33, 34 are designed for radiographs of the head region. They can of course also be used for other body regions and must then be accordingly sized and mounted.

Figure 8:
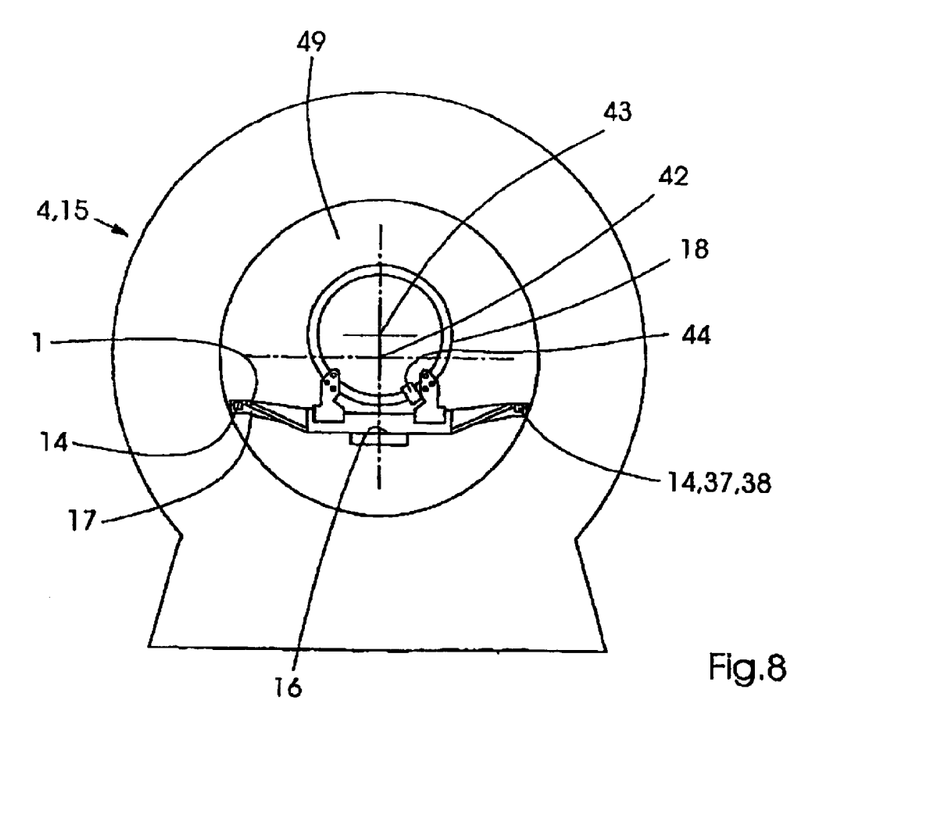
FIG. 8 shows a magnetic resonance tomograph with an inventive stretcher without adapter plates.

FIG. 8 shows a magnetic resonance tomograph 15 with a tubular opening 49, into which a stretcher 1 is introduced. The stretcher 1 has sliding rails 38 which extend in corresponding grooves 37. The positioning means 5' of the cart 2 which can be displaced in a longitudinal direction suitably corresponds to a corresponding positioning means 14 of the magnetic resonance tomograph 15 such that the stretcher 1 can be inserted directly by the cart 2 into the magnetic resonance tomograph 15. At least one dove-tailed guide is also advantageous in this case. For the above-mentioned reasons, the stretcher 1 is separately introduced since in the present case, the magnetic resonance tomographs 15 already contains a stretcher 17 which is not removed when the stretcher 1 is introduced. The small vertical extent of the stretcher 1, which is inserted without adapter plate 3, causes only slight elevation of the position of the patient and a head holder mounting 16 with a head holder ring 18 can be mounted such that the center 43 of the head holder ring 18 is in the region of the center 42 of the magnetic resonance tomograph 15. As illustrated, the separation between the two centers 42 and 43 is sufficiently small that the image is still acceptable since the head is not located outside of the region of high quality imaging. Conventional holding stops 44 for fixing a head are also shown.

Figure 9:
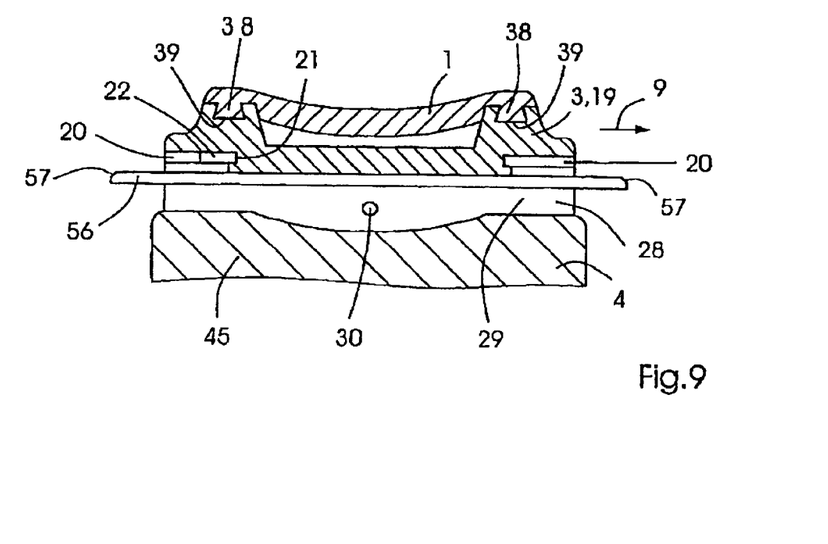
FIG. 9 shows a sectional view of an adapter part.
Figure 10:
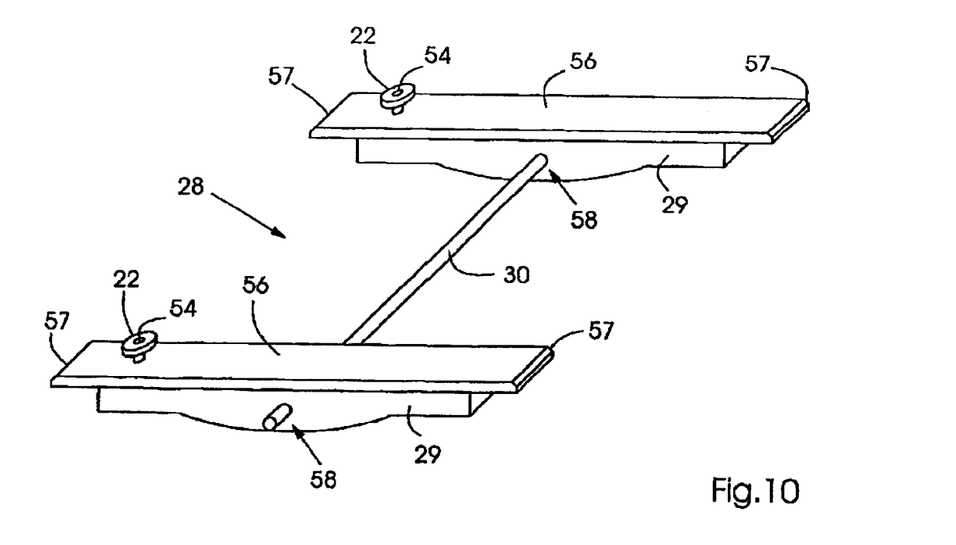
FIG. 10 shows a perspective view of the adapter part.

FIG. 9 shows a cross-section through an adapter part 28. It is particularly advantageous when diagnosis or treatment stations 4 have stretchers 45 which may have very different shapes. In this case, the adapter part 28 is formed of at least two support bars 29 which are connected to at least one bar 30 (shown in perspective view in FIG. 10). The intermediate plate 19 can be disposed directly on this adapter part 29 or preferably—as shown—onto a positioning board 56. Devices 10 for exact positioning may also be provided. The positioning means 10 and the positioning means 5" correspond to the description of FIGS. 3 and 4 with the exception that the diagnosis and treatment station 4 is not directly provided with guiding and holding bolts 22, rather the adapter part 28. The other functions are identical to those described in FIGS. 3 and 4. The support bars 29 are provided with clamping devices 58 to be able to freely position and then fix them on the at least one bar 30. Bevels 57 in the positioning boards 56 permit sliding of the intermediate plate 19 without being hindered by a projecting edge. Of course, several support bars 29 may be provided. The advantage of this adapter part 28 is that the support bars 29 may be appropriately formed without difficulties and can be adjusted to the different shapes of existing stretchers 45.

The illustrations are merely a small preferred selection of embodiments of the invention. It is important that the designs of the stretcher 1 and the adapter plates 3 depend on the various diagnosis or treatment stations 4.

As shown above, the stretcher 1 with intermediate plate 19 and base plate 11 is disposed onto an operating table 12, wherein a liftable positioning means 5, 50 is provided on the cart 2 and on the operating table 12.

Only the stretcher 1 is introduced into the magnetic resonance tomograph 15 by means of a longitudinally displaceable positioning means 5", wherein the material of the stretcher must be completely non-magnetic and non-conducting.

Computer tomography and angiography devices usually require transverse displacement of the stretcher 1 with intermediate plate 19. The precondition for insertion into a computer tomography device is that the above-mentioned components 1, 19 contain no metal. These devices advantageously have corresponding positioning means 5" which can be displaced in a transverse direction to be able to position the intermediate plate 19 with stretcher 1 directly in the devices. Towards this end and for insertion into further diagnosis or treatment stations 4, such as magnetic resonance tomographs 15, the cart 2 may also have means for height adjustment.

The stretcher 1 is usually inserted into a radiation device together with the base plate 11 and intermediate plate 19 in the same manner as for the operating table 12. Positioning means 5 for lifting are also provided in this case.

This is of course only an exemplary enumeration of diagnosis or treatment stations 4, and positioning means 5, 5', 5", 50, further diagnosis or treatment stations 4 and also other embodiments of the above-mentioned positioning means 5, 5', 5", 50 may be adjustable to the existing diagnosis or treatment stations 4. Additional diagnosis or treatment stations 4 can also be adapted to permit displacement of the stretcher 1, or of one of the adaptor plates 3, from the cart 2 directly into the respective diagnosis or treatment station 4 while thereby providing stops and further positioning devices for the respective exact positioning.

Markings can and should be provided on fixing devices such as e.g. the head holder ring 18 or to adapted shells for the corresponding body parts to examine the positioning in the individual diagnosis or treatment stations 4 and to provide fine positioning. Corresponding conventional methods and devices are hereby incorporated by reference.

List of Reference Numerals

1 Stretcher
2 Cart
3 Adapter plates
4 Diagnosis or treatment stations
5,5',5" Positioning means
5 Liftable positioning means
5' Longitudinally displaceable positioning means
5" transversely displaceable positioning means
6 Arrow:lift
7 Arrow:lower
8 Arrow:displacement in the longitudinal direction
9 Arrow:displacement in the transverse direction
10 Positioning devices
11 Base plate
12 Operating table
13 Height adjustment means
14 Positioning means in a magnetic resonance tomograph
15 Magnetic resonance tomograph
16 Head holder mounting
17 Stretcher of a magnetic resonance tomograph
18 Head holder ring
19 Intermediate plate
20 Guides (T-shaped groove)
21 End stops
22 Guiding and holding bolts
23 Head end of the cart
23 ' Head end of the stretcher
24 Springs
25 Wheel brake
26 Fixing of the front wheels
27 Front wheels
28 Adapter part
29 Support bars
30 Bar
31 Floor
32 Position fixation means
33 Vertical X-ray cassette holder
34 Horizontal X-ray cassette holder
35 Front side of the cart
36 Portal-like opening
37 Groove
38 Sliding rail
39 Tapering
40 Leg of the operating table
41 Fixation mounted to the floor
42 Center of the magnetic resonance tomograph
43 Center of the head holder ring
44 Holding stop for fixing a head
45 Existing stretcher of a diagnosis or treatment station
46 Bolt
47 Locating holes
48 Cavity
49 Tubular opening
50 Further positioning means
51 Handles
52 Thread for guiding and holding bolts
53 Locating holes for locating pins
54 Locating holes in guiding and holding bolts
55 Locating pins
56 Positioning board
57 Bevel
58 Clamping device

What is claimed is:

1. A system for positioning and transporting a patient to a first diagnosis or treatment station and to a second diagnosis or treatment station, the system comprising:
   a transportable stretcher for the patient;
   a cart for transporting said stretcher with the patient; and
   at least one adapter plate, said at least one adapter plate having first means for connecting said adapter plate to said stretcher, second means for connecting said adapter plate to said cart, third means for connecting said adapter plate to the first diagnosis or treatment station and fourth means for connecting said adapter plate to the second diagnosis or treatment station.

2. The system of claim 1, wherein said stretcher is structured for separate movement back and forth between said cart and the at least one diagnosis or treatment station.

3. The system of claim 2, wherein said at least one adapter plate is structured to move said stretcher, together with said adapter plate, to and from the at least one further diagnosis or treatment station.

4. The system of claim 1, wherein at least one of said stretcher and the at least one adapter plate comprises positioning means for lifting and precise lowering.

5. The system of claim 1, wherein at least one of said stretcher and the at least one adapter plate comprises positioning means for displacement in a longitudinal direction.

6. The system of claim 1, wherein at least one of said stretcher and the at least one adapter plate comprises positioning means for displacement in a transverse direction.

7. The system of claim 1, wherein at least one of said stretcher and said at least one adapter plate comprises positioning devices for defined, secure disposition.

8. The system of claim 7, wherein said cart comprises positioning devices for defined, secure disposition.

9. The system of claim 1, wherein at least one or said stretcher and said at least one adapter plate comprises positioning means to prevent inadvertent lifting.

10. The system of claim 1, wherein at least one of said cart, said stretcher, and said at least one adapter plate comprises materials selected to avoid disturbances to the diagnosis or treatment station with which the system interacts.

11. The system of claim 10, wherein said cart and said at least one adapter plate consist essentially of non-magnetic or weakly magnetic materials.

12. The system of claim 10, wherein said stretcher consists essentially of non-magnetic and non-conducting materials.

13. The system of claim 10, wherein said stretcher and said at least one adapter plate contain essentially no metal.

14. The system of claim 1, wherein said at least one adapter plate is structured for secure mounting to the first and the second diagnosis or treatment stations.

15. The system of claim 1, wherein said at least one adapter plate is a base plate which can be disposed in a secure fashion on said cart and which can be lifted therefrom.

16. The system of claim 15, wherein said cart is designed for movement together with said base plate over the at least one diagnosis or treatment station to cooperate with further positioning means and height adjustment means disposed on that station for moving said base plate and said stretcher to and from said cart, wherein said cart can be removed from the diagnosis or treatment station after lifting said base plate.

17. The system of claim 1, wherein the first diagnosis or treatment station is an operating table.

18. The system of claim 1, wherein said stretcher comprises at least one positioning device which can be fixed to said stretcher to secure body parts which are to be treated.

19. The system of claim 18, wherein a head holder mounting is disposed at an end of said stretcher.

20. The system of claim 19, wherein said head holder mounting also serves as a positioning stop to end longitudinal displacement.

21. The system of claim 19, wherein said head holder mounting is structured, disposed, and dimensional to position a holder ring for locating a head of the patient in a central region of a magnetic resonance tomograph, despite disposition of said stretcher above a stretcher of that magnetic resonance tomograph.

22. The system of claim 15, wherein an adapter plate is provided as an intermediate plate between said stretcher and said base plate.

23. The system of claim 22, wherein said intermediate plate has a positioning means which can be displaced transversely with respect to said base plate.

24. The system of claim 23, wherein said intermediate plate transverse positioning means consists essentially of guides which are structured to prevent lifting of said intermediate plate and end stops for positioning.

25. The system of claim 23, wherein said intermediate transverse positioning means permits displacement to one side and has end stops on en other side.

26. The system of claim 23, wherein said intermediate plate transverse positioning means has guides which widen towards an outside and taper towards an end stop.

27. The system of claim 26, wherein at least two guides with end stops are provided on each side.

28. The system of claim 27, wherein said end stops are produced through cooperation between end regions of said guides and guiding and holding bolts.

29. The system of claim 28, wherein said intermediate plate can optionally be displaced to one or an other side by removing and fixing said guiding and holding bolts.

30. The system of claim 28, wherein the system is structured to dispose said base plate at a same height as a diagnosis or treatment station to position said stretcher using guiding and holding bolts of the station, up to stops ending transverse displacement thereof.

31. The system of claim 1, wherein said cart comprises springs at least at a head end thereof.

32. The system of claim 1, wherein said cart has a wheel brake and means for fixing front wheels in a direction of travel.

33. The system of claim 1, further comprising at least one further adapter plate for positioning said stretcher on a diagnosis or treatment station for which none of said at least one adapter plate fits.

34. The system of claim 33, wherein said adapter part creates a support on an existing stretcher.

35. The system of claim 33, wherein said adapter part comprises at least two support bars which can be connected to each other by at least one additional bar.

36. The system of claim 30, further comprising at least one further adapter part for positioning said stretcher on the diagnosis or treatment station said adapter part having guiding and holding bolts to provide the diagnosis or treatment station with end stops.

37. The system of claim 17, wherein the operating table has a synchronous electric height adjustment comprising a device which, after each actuation of a height adjustment, disconnects a power supply from mains and reconnects same only upon explicit command.

38. The system of claim 17, wherein the operating table is structured for positioning in a secure but liftable fashion through cooperation with a position fixation mounted to a floor.

39. The system of claim 17, wherein the operating table is provided with vertically and horizontally disposed X-ray cassette holders.

40. The system of claim 1, wherein said stretcher and said at least one adapter plate have a tapering at head ends thereof.

41. The system of claim 1, wherein said at least one adapter plate is individually structured to cooperate with existing diagnosis or treatment stations.

42. The system of claim 1, wherein said cart comprises means for height adjustment.

43. The system of claim 1, wherein said at least one adapter plate comprises a first adapter plate having said third connecting means and a second adapter plate having said fourth connecting means.

44. A system for positioning and transporting a patient to at least one diagnosis or treatment station, the system comprising:
- a transportable stretcher for the patient;
- a cart for transporting said stretcher with the patient; and
- at least one adapter plate, wherein said stretcher, said cart and said adapter plate are structured for connection to each other and designed such that said stretcher, with the patient, can be moved back and forth between said cart and the at least one diagnosis or treatment station, wherein said stretcher comprises positioning means for displacement in a longitudinal direction.

45. The system of claim 44, wherein said stretcher longitudinal displacement means is designed to prevent lifting of said stretcher.

46. The system of claim 44, wherein said stretcher longitudinal displacement means is structured to cooperate with positioning means on the diagnosis or treatment station such that said stretcher can be inserted from said cart directly into or onto the diagnosis or treatment station.

47. The system of claim 10, wherein said stretcher longitudinal displacement means is structured to cooperate with positioning means of a magnetic resonance tomograph.

48. The system of claim 47, wherein said stretcher is flat and can be pushed over a magnetic resonance tomograph stretcher in cooperation with positioning means of the magnetic resonance tomograph disposed and designed towards this end.

49. A system for positioning and transporting a patient to at least one diagnosis or treatment station, the system comprising:
- a transportable stretcher for the patient;
- a cart for transporting said stretcher with the patient; and
- at least one adapter plate, wherein said stretcher, said cart and said adapter plate are structured for connection to each other and designed such that said stretcher, with the patient, can be moved back and forth between said cart and the at least one diagnosis or treatment station, wherein said cart has a portal-like opening at a front side thereof for movement of said cart over the diagnosis or treatment station to accept said stretcher with said at least one adapter plate.

* * * * *

UNITED STATES PATENT AND TRADEMARK OFFICE
CERTIFICATE OF CORRECTION

PATENT NO. : 6,928,672 B2  
APPLICATION NO. : 10/478595  
DATED : August 16, 2005  
INVENTOR(S) : Otto Pastyr et al.

Page 1 of 1

It is certified that error appears in the above-identified patent and that said Letters Patent is hereby corrected as shown below:

On the Title Page, Item (75)

Please correct the last name of the second inventor to replace "Schlegei" with -- Schlegel --.

Item (73) Assignee is added:

-- Deutsches Krebsforschungszentrum  
Stiftung des Oeffentlichen Rechts,  
Heidelberg, Germany --.

Signed and Sealed this

Twentieth Day of October, 2009

David J. Kappos  
*Director of the United States Patent and Trademark Office*